United States Patent [19]
Roussilhe et al.

[11] Patent Number: 5,942,379
[45] Date of Patent: Aug. 24, 1999

[54] 3-PYRAZOLIDONE COMPOUNDS AND PHOTOGRAPHIC DEVELOPER SOLUTIONS CONTAINING SAME

[75] Inventors: Jacques Roussilhe, Virey Le Grand, France; Siu C. Tsoi, Hertfordshire, United Kingdom

[73] Assignee: Eastman Kodak Company, Rochester, N.Y.

[21] Appl. No.: 09/010,302

[22] Filed: Jan. 21, 1998

Related U.S. Application Data

[63] Continuation-in-part of application No. 08/694,792, Aug. 9, 1996, abandoned.

[30] Foreign Application Priority Data

Aug. 10, 1995 [FR] France ........................... 9509850

[51] Int. Cl.⁶ .................................................. G03C 5/305
[52] U.S. Cl. .......................................... 430/480; 430/483
[58] Field of Search .................................. 430/480, 483

[56] References Cited

U.S. PATENT DOCUMENTS

| | | | |
|---|---|---|---|
| 2,743,279 | 4/1956 | Reynolds et al. | 260/310 |
| 3,938,997 | 2/1976 | Fisch et al. | 430/468 |
| 4,266,002 | 5/1981 | McCreary et al. | 430/218 |
| 5,098,819 | 3/1992 | Knapp | 430/436 |
| 5,236,816 | 8/1993 | Purol et al. | 430/492 |
| 5,264,323 | 11/1993 | Purol et al. | 430/264 |
| 5,384,232 | 1/1995 | Bishop et al. | 430/440 |

FOREIGN PATENT DOCUMENTS

| | | |
|---|---|---|
| 461783 | 12/1991 | European Pat. Off. . |
| 588408 | 3/1994 | European Pat. Off. . |
| 603586 | 6/1994 | European Pat. Off. . |
| 96420267.5 | 8/1996 | European Pat. Off. . |
| 2737722 | 8/1995 | France . |
| 1025575 | 4/1966 | United Kingdom . |
| 95/00881 | 1/1995 | WIPO . |

OTHER PUBLICATIONS

Chem. Abstracts vol. 73(6) Aug. 10, 1970, 30672v.
Beilstein Database BRN 656444, 664541, 665339.

*Primary Examiner*—Hoa Van Le
*Attorney, Agent, or Firm*—J. Lanny Tucker

[57] ABSTRACT

The present concerns compounds of the 3-pryazolidone type comprising solubilizing groups which are not directly attached to the phenyl ring or to the pyrazolidino ring. These compounds can be used as co-developing agents in the development of black and white photographic products.

8 Claims, 6 Drawing Sheets

FIG. 6

3-PYRAZOLIDONE COMPOUNDS AND PHOTOGRAPHIC DEVELOPER SOLUTIONS CONTAINING SAME

RELATED APPLICATION

This is a Continuation-in-part of U.S. Ser. No. 08/694,792, filed Aug. 9, 1996.

FIELD OF THE INVENTION

The present invention concerns photography and novel compounds of the 3-pyrazolidone type which can be used in silver halide photographic developer solutions. These compounds have use, in particular, as co-developers for developing black and white photographic papers or films.

BACKGROUND OF THE INVENTION

Developing agents are described in *Chimie et Physique Photographiques,* P Glafkides, Chapter IX, pages 152–170, fifth edition. In general, a principal developing agent is used in association with an auxiliary developing agent. A synergistic effect is observed between the principal developing agent, hereinafter referred to as the "developing agent", and the auxiliary developing agent or "co-developing agent" when the combined activity of the mixture of these two agents is greater than the sum of the activities of each of these agents used separately in the same solution. This phenomena, referred to as "superadditivity" is explained in Mason *"Photographic Processing Chemistry"*, Focal Press, London, 1975.

Di- and polyhydroxyphenols (for example, hydroquinone) and reductones (for example, compounds of the ascorbic acid type) are the developing agents which are most used in practice in black and white developing solutions.

Among the most often used co-developing agents are aminophenols, such as ELON® (methyl-p-aminophenol sulfate), 1-phenyl-3-pyrazolidones or phenidones, such as phenidone-A (1-phenyl-3 pyrazolidone), phenidone-B (1-phenyl-4 methyl-3-pyrazolidone), dimezone (1-phenyl-4-4'-dimethyl-3-pyrazolidone) or dimezone-S (1-phenyl-4-methyl-4'-hydroxymethyl-3-pyrazolidone). Additional representative examples of aminophenols and phenidones are described in U.S. Pat. No. 2,688,549, U.S. Pat. No. 2,691,589, U.S. Pat. No. 3,865,591, U.S. Pat. No. 4,269,929, U.S. Pat. No. 4,840,879 and U.S. Pat. No. 5,236,816, and by G. E. Ficken and B. G. Sanderson, *The Journal of Photographic Science,* Vol 11, 1963, pages 157–164.

These co-developing agents have low solubility in water, which presents drawbacks with regard to the manufacture of the developer and its ease of use. In addition, photographic processing solutions are often in the form of powders to be dissolved in water or liquid concentrates to be diluted before use. These powders must be easy to solubilize and the co-developing agents must be sufficiently soluble to enable concentrates to be formulated.

EP-A-528,480 describes a radiographic product comprising a 3-pyrazolidone substituted by a carboxy group directly attached to the phenyl ring. This compound is used as an anti-fogging agent. The radiographic product is developed with a conventional developer comprising hydroquinone and a 1-phenyl-pyrazolidone-1-one co-developing agent.

The problem of the low solubility of phenidone or dimezone-S was resolved in U.S. Pat. No. 4,753,869 by preparing these 1-phenyl-3-pyrazolidones in the form of salts of four particular acids including sulfo groups which dissolve easily in water and are stable during storage. The activity of these compounds in combination with hydroquinone is said to be comparable with that of pyrazolidones which are not in the form of salts.

*Zhurnal Nauchnoi i Prikladnoi Fotografii i kinematografii* 10, (5), 321–329 (1963) by V. L. Abritalin et al describes photographic developers comprising hydroquinone and a large number of derivatives of 3-pyroazolidones, some of which carry solubilizing groups on the benzene ring. It describes the introduction of the carboxy or sulfo solubilizing groups on the benzene ring to bring a significant reduction in superadditivity. This tendency is also noted by G. E. Ficken and B. G. Sanderson in *The Journal of Photographic Science,* Vol. 11, 1963, pages 157–160, who report that the introduction of a carboxylic group on the phenidone reduces the superadditivity between phenidone and hydroquinone.

Hydroquinone-based developers generally give good results but present drawbacks with regard to health and the environment. This is why ascorbic acid is used in place of hydroquinone in association with phenidones in developer compositions described in many patents.

Among them, U.S. Pat. No. 5,098,819 describes a developer composition comprising ascorbic acid or its derivatives, and a 3-pyrazolidone compound. The developing agent in the examples contains sodium erythorbate, phenidone or dimezone-S and potassium carbonate. This developer composition is less toxic than those containing hydroquinone and caustic bases and the sensitometric results are close to those obtained with compositions containing hydroquinone.

U.S. Pat. No. 3,938,997 describes a developer solution for the fast development of high-contrast products of the microfilm type. These solutions comprise three developing agents: the first is a ferrous chelate, the second is a compound of the ascorbic acid type, the third is phenidone, GLYCINE®, hydroxylamine sulfate, etc. Developer solutions are obtained which can be easily concentrated.

EP-A-588,408 describes a developer comprising a principal developing agent of the ascorbic acid type and a mixture of two co-developing agents of the phenidone type selected from phenidone-A, phenidone-B and dimezone, dimezone-S. This developer composition makes it possible to obtain improved sensitometric stability which does not depend on the reduction in the pH observed during continuous processing without regeneration. The examples concern emulsions for microfilms.

U.S. Pat. No. 5,264,323 describes compositions for the development of films for graphic arts comprising ascorbic acid or its isomers and a 3-pyrazolidone or aminophenol compound.

EP-A-461,783 describes a developer composition comprising ascorbic acid or its derivatives, a 3-pyrazolidone compound, sulfite or bisulfite and sodium sulfate or glutaraldehyde, that can be used for the development of medical radiographs.

WO 95/00881 describes stable developers comprising a developing agent of the ascorbic acid type or a sugar-type derivative of this acid, and a co-developing agent selected from phenidones and aminophenols (or a mixture of these) for the fast development of graphic arts films incorporating compounds of the hydrazine type.

U.S. Pat. No. 5,384,232 describes developer compositions comprising sodium erythorbate or erythorbic acid associated with dimezone-S for developing lithographic films.

EP-A-603,586 describes formulations of concentrates for developers incorporating a compound of the ascorbic acid type and a co-developer, preferably dimezone-S.

British Patent 1,025,575 describes 1-aryl-3-pyrazolidone developing agents having a 4-$CH_2CO_2H$ substituent. While these compounds are reported to have less activity than the unsubstituted corresponding 1-aryl-3-pyrazolidone, their water solubility make them valuable to prepare developers from powdered compositions.

Soviet Patent 265,715 describes a 1-aryl-3-pyrazolidone developing agent with a para-$CH_2CH_2CO_2H$ group on the 1-aryl substituent. The 4-position of the pyrazolidone nucleus is unsubstituted.

SUMMARY OF THE INVENTION

The present invention provides an aqueous developer solution for developing silver halide photographic materials, comprising a silver halide developing agent selected from reductones and compounds of the hydroquinone type, and at least one co-developing agent which is a compound of the formula I:

(I)

wherein

$R_1$ and $R_2$ are independently alkyl, or a group represented by the formula II:

—$(CH_2)_m$—$(L)_n$—A—(Sol)

wherein m is an integer of 0 to 5, and n is 0 or 1,

L is a divalent group selected from wherein $R_8$ is $R_9$ or —A—(Sol), $R_9$ is hydrogen, alkyl or aryl;

A is a divalent group selected from wherein q is an integer from 0 to 5, and y is an integer from 1 to 3;

(Sol) is a solubilizing group selected from:

—$CO_2H$, —$SO_3H$, —$NHSO_2R_{10}$, —$SO_2NH_2$, —$SO_2NHR_{10}$, polyhydroxyalkyl, wherein $R_{10}$ is alkyl or aryl, $R_{11}$ is hydroxy, alkyl or aryl and $R_{12}$ is hydrogen, alkyl or aryl;

$R_3$ to $R_7$ in formula (I) are independently hydrogen, substituted or unsubstituted alkyl, substituted or unsubstituted alkoxy, substituted or unsubstituted aryloxy, or a group represented by the formula:

wherein p is 0 or 1;

X is a divalent group selected from —O—, —S— and —$NR_8$—; and m, L, n, A, (Sol) and $R_8$ are as defined above, provided that at least one of $R_1$ to $R_7$ comprises Sol.

Thus, one of the objects of the present invention is to use compounds of the 3-pyrazolidone type as co-developing agents, such compounds having improved solubility without the superadditivity effect and the stability being degraded.

The compounds described above have improved solubility compared with known phenidones. Surprisingly, the presence of these solubilizing groups which are not directly attached to the phenyl ring or to the pyrazolidino ring do not cause an appreciable reduction in superadditivity. On the contrary, the developer solutions comprising these compounds as co-developing agents have a satisfactory photographic activity.

In addition the developer solutions according to the invention containing a developing agent of the ascorbic acid type have little tendency to form silver sludge or to cause the deposition of metallic silver on the equipment.

BRIEF DESCRIPTION OF THE DRAWINGS

In the following description, reference will be made to the following FIGURES.

DETAILED DESCRIPTION OF THE INVENTION

Black and white photographic products can be considered to form two distinct groups according to the development time. Thus black and white films for photography and cinema, industrial radiographs and black and white papers are developed relatively slowly. Typical development times are around 1 to 3 minutes for papers and 4 to 12 minutes for films. The development temperature is between 18 and 27° C. but can also be higher. This is what is referred to in the art as a long access time or "slow access" type. A known developer of the "slow access" type is the KODAK D-76® powder universal developer used for example for the development of black and white photographic films and which comprises hydroquinone and ELON®.

Rapid development systems, also referred to as "short access time" or "rapid access" types, are used for the development of medical radiographs, graphic arts and microfilms. These products are developed with highly active solutions. The development time is around 30 seconds or less and the development temperature is approximately 35° C. An example of a developer of the "rapid access" type is the KODAK RP X-OMAT® developer, used for the development of films for medical radiography, which comprises hydroquinone and phenidone-A as a co-developing agent. Other "rapid access" developers comprising ascorbic acid and dimezone-S as a co-developing agent are described in *Research Disclosure* of August 1993, Article 35249.

The compounds of the 3-pyrazolidone type useful in this invention have a fully substituted 4 position on the 3-pyrazolidone ring and solubilizing groups which are not directly attached to the phenyl ring or to the pyrazolidino.

According to one embodiment, the 3-pyrazolidones of the invention have the formula I:

I wherein $R_1$, $R_2$ represent an alkyl radical, a substituted alkyl radical where at least one of $R_3$ to $R_7$ is defined above where A represents or phenylene; and

1) p, m and n are each 0, or
2) only p and m are 0 and L represents wherein each of $R_8$ and $R_9$ is hydrogen. Useful compounds as represented by the above formula are for instance:

(1)

(2)

-continued (3)

(4)

(5)

(6)

(7)

-continued

(8)

(9)

(10)

(11)

-continued (12)

Further 3-pyrazolidone compounds according to the invention can be represented by the formula:

wherein m, L, A, Sol, $R_1$ are as defined above, and $R_3$–$R_7$ are independantly alkyl, substituted alkyl, alkoxy or substituted alkoxy. Examples of such compounds are:

(13)

(14)

-continued (15)

(16)

The invention concerns developer solutions comprising a developing agent for silver halides selected from di- and poly-hydroxybenzenes and reductones, and at least one co-developing agent that is one of the novel compounds as defined above.

The compounds described above can be used as the sole co-developing agent or else in mixture with other compounds such as aminophenols or phenidones (such as ELON®, Phenidone-A, Phenidone-B, Dimezone, Dimezone-S or 4,4-bis(hydroxymethyl)-1-phenyl-3-pyrazolidinone). In general terms, developing agents that can be used are described in *Research Disclosure,* publication 36544, September 1994, Chapter XIX, page 536.

In practice, use is made of a quantity of co-developing agent of the 3-pyrazolidone type in the developer composition of between 0.0005 and 0.2 mol/l, and preferably between 0.001 and 0.006 mol/l of ready-to-use solution.

The compounds of the 3-pyrazolidone type according to the invention can be used in developer compositions as co-developing agents for "slow access" or "rapid access" processes in combination with all known developers.

In black and white developer solutions, the developing agent is a compound preferably selected from di- and poly-hydroxybenzenes and reductones. The dihydroxybenzenes most often used are hydroquinone, catechol and derivatives thereof. Examples of reductones include ene-diols, ene-aminols, ene-diamines, thio-enols and enamine-thiols. The reductones most often used are cited in U.S. Pat. No. 2,691,589, in particular ascorbic acids, its stereoisomers, diastereoisomers and sugar-type derivatives.

Hydroquinone can be used as a developing agent in the developer solutions but, in order to preserve the environment, ascorbic acid, its sugar-type derivatives, stereoisomers, diastereoisomers, precursors of these acids and their salts are preferred to this.

For example, use can be made of D-isoascorbic (or erythorbic) acid, L-ascorbic acid and their salts such as sodium or potassium ascorbate or erythorbate; sugar-type derivatives of ascorbic acid, for example D-glucoascorbic acid, 6-desoxy-1-ascorbic acid, L-rhamnoascorbic acid, L-fucoascorbic acid, D-glucoheptoascorbic acid, sorboascorbic acid, ω-lactoascorbic acid, maltoascorbic acid, L-araboascorbic acid, L-glucoascorbic acid, D-galactoascorbic acid, L-guloascorbic acid and L-alloascorbic acid, and imino-L-ascorbic acid; cetal derivatives of L-ascorbic and D-isoascorbic acids, for example 5,6-isopropylene ascorbic acid; and ascorbic acid precursors, for example methyl-2-cetogluconate or a mixture of these.

In practice, a quantity of developing agent of the hydroquinone or ascorbic acid type in the developer solution of between 0.05 and 0.4 mol/l and preferably between 0.15 and 0.30 mol/l of ready-to use solution is used.

The preferred developing compositions comprise a developing agent selected from ascorbic acid, sugar-type derivatives of ascorbic acid, stereoisomers, diastereoisomers, precursors of these acids and their salts and at least one co-developer which is one of the novel compounds of the 3-pyrazolidone type according to the invention.

The developers according to the invention may contain, in addition to the developing agent and co-developing agent, many conventional additives such as solvents for silver halides, alkaline bases, organic or inorganic anti-fogging agents, pH buffering agents, antioxidants, sequestering agents, agents for controlling swelling, hardening agents and wetting agents. Within the scope of the invention, the developer composition is open to many variations that would be obvious to one skilled in the art. These developers can be concentrated in liquid form or in the form of powders that must be dissolved in water in order to obtain the ready-to-use solution.

These developing solutions according to the invention are useful for developing black and white products, such as products for the graphic arts, radiographic products, black and white photographic films and papers or microfilms or for the black and white development stage of color reversible films and papers.

The invention is illustrated by the following examples:

EXAMPLE 1

Synthesis of the Compound (4-Methyl-3-oxo-1-phenylpyrazolidin-4-yl)methyl 2-sulphobenzoate (Compound 12)

To a suspension of 4-methyl-4-hydroxymethyl-1-phenyl-3-pyrazolidinone (dimezone-S) (10 g, 48.5 mmol) in dry acetonitrile (200 ml), was added 2-sulfobenzoic acid cyclic anhydride (8.9 g, 48.5 mmol) in a single portion at room temperature with stirring. The reaction mixture was heated to reflux under nitrogen until complete dissolution was observed. The reflux was continued for 24 hours and the mixture was cooled in an ice/water bath for 2 hours. A solid precipitate was obtained which was recovered by filtration and washed with ice cooled acetonitrile. After drying under vacuum, 17.9 g (95%) of 4-methyl-3-oxo-1-phenyl-pyrazolidin-4-yl)methyl 2-sulfobenzoate (Compound II) were isolated as an off-white solid.

EXAMPLE 2

Synthesis of the Compound {1-(3,4-dimethylphenyl)-4-methyl-3-oxo-pyrazolidin-4-yl}methyl 2-sulfobenzoate (Compound 14)

To a suspension of {1-(3,4-dimethylphenyl)-4-hydroxymethyl-4-methyl-3-pyrazolidinone (10.0 g, 42.74 mmol) in dry acetonitrile (200 ml), was added 2-sulfobenzoic acid cyclic anhydride (7.86 g, 42.74 mmol) in a single portion at room temperature with stirring. The reaction mixture was heated to reflux under nitrogen for 22 hours until complete dissolution was observed. After cooling the mixture to room temperature, a heavy precipitate formed, which was recovered by filtration with suction. After washing with acetonitrile and drying under vacuum, 13.7 g (77%) of {1-(3,4-dimethylphenyl)-4-methyl-3-oxo-pyrazolidin-4-yl}methyl 2-sulfobenzoate (Compound III) were isolated in the form of a pale pink solid.

EXAMPLE 3

Synthesis of the Compound {1-(3,4-dimethoxyphenyl)-4-methyl-3-oxo-pyrazolidin-4-yl}methyl 2-sulfobenzoate (Compound 16)

To a suspension of {1-(3,4-dimethoxyphenyl)-4-hydroxymethyl-4-methyl-3-pyrazolidinone (1.0 g, 3.76 mmol) in dry tetrahydrofuran (20 ml) was added 2-sulfobenzoic acid cyclic anhydride (0.69 g, 3.76 mmol), in a single portion at room temperature with stirring. The reaction medium was heated to reflux under nitrogen for 24 hours until complete dissolution was observed. The mixture was cooled in a ice/water bath and the solid was recovered by filtration and washed with acetonitrile. After drying under vacuum, 0.93 g (55%) of {1-(3,4-dimethoxyphenyl)-4-methyl-3-oxo-pyrazolidin-4-yl}methyl 2-sulfobenzoate (Compound IV) was isolated in the form of a pale yellow solid.

EXAMPLE 4

Synthesis of 2-(4-(4,4'-dimethyl-3-oxo-pyrazolidinyl)phenyl) acetic acid (Compound 1)

To a suspension of 4-nitrophenylacetic acid (14.9 g, 0.1 mol) and benzyl alcohol (12 g, 0.11 mol) in 230 ml of toluene, p-toluene sulphonic acid monohydrate (0.5 g) were added at room temperature whilst stirring. The solution was heated to reflux under Dean and Stark conditions for around 22 hours. The solvent was eliminated under reduced pressure and the residual solid was recrystallised in a mixture of toluene and petroleum. After vacuum drying, 21 g (77.5%) of benzyl 4-nitrophenyl acetate (compound 1a) was isolated in the form of a whitish solid.

A suspension of compound (1a) (5 g, 18.45 mmol) was heated in a mixture of acetic acid (45 ml) and water (5 ml) over a steam bath until the solid dissolves. Iron powder (6 g, 105 mmol) was added in portions over a period of around 10 minutes. Heating was continued for another 1.5 hours after the end of the addition. The hot reaction mixture was poured into water (200 ml) whilst rapidly stirring, and the mixture was extracted in its entirety with some ethyl acetate (2×200 ml). The combined organic extracts were washed with brine (200 ml) and dried on magnesium sulphate and the solvent was evaporated under reduced pressure in order to obtain a yellow oil (5.8 g). The raw product is dissolved in acetonitrile (70 ml) and gaseous HCl was bubbled into the solution to saturation point. The solid was collected by filtration and was dried under vacuum in order to obtain 3.4 g (65.4%) of benzyl 4-aminophenylacetate hydrochloride (compound 1b) in the form of a cream-coloured solid.

A suspension of compound (1b) (7.9 g, 28.5 mmol) in a mixture of concentrated HCl (32 ml) and water (11 ml) was cooled to 0° C. A solution cooled in sodium nitrite ice (2.2 g, 31 mmol) in water (6.5 ml) is added to the above suspension for a period of 15 minutes, keeping the internal temperature below 5° C. The mixture was stirred for 10 minutes more before adding a mixture of tin II chloride (23.8 g, 126.2 mmol), concentrated HCl (130 ml) and water (260 ml) at room temperature, stirring rapidly. The solid obtained was collected by filtration and the moist solid was titrated with acetonitrile (150 ml), filtered and dried under vacuum in order to obtain 5.9 g (71%) of benzyl 4-hydrazinophenylacetate hydrochloride (compound 1c).

To a solution of compound (1c) (7.7 g, 26.3 mol) in dry pyridine (60 ml), 3-chloropivaloyl chloride (4.0 g, 25.5 mol) were added dropwise for 10 minutes at around 5° C. with stirring. The mixture was then stirred at room temperature for 20 hours before being poured into a mixture of ice and water (600 ml) and concentrated HCl (60 ml). A yellow solid was collected by filtration, washed with water and dried under vacuum on phosphorus pentoxide (8.4 g). The raw product is titrated with cold diethyl ether (80 ml), filtered and dried in air in order to obtain 7.2 g (81%) of benzyl 2-(4-(4,4'-dimethyl-3-oxo-pyrazolidinyl) phenyl acetate (compound 1d) in the form of a cream-coloured solid.

A solution of compound (1d) (3.5 g, 10.35 mmol) was hydrogenated on palladium-containing carbon (0.3 g, 10% Pd) in tetrahydrofuran (270 ml) under 34 atmospheres of hydrogen at room temperature for 24 hours. The catalyst was eliminated by filtration on kieselguhr and the filtrate evaporated under reduced pressure in order to obtain a yellow gum. The raw product was titrated with diethylether (100 ml), filtered and dried under vacuum. 2.13 g (83%) of 2-(4-(4,4'-dimethyl-3-oxo-pyrazolidinyl)phenyl) acetic acid (compound 1) is obtained in the form of a cream-coloured solid.

EXAMPLE 5

Synthesis of Compound 5

3-Chloropivaloyl chloride (18.1 g, 116.5 mmol) was added to a suspension of 3-nitrophenylhydrazine hydrochloride (22.1 g, 116.5 mmol) in anhydrous pyridine (250 ml). The addition was carried out at 5° C. with stirring. This addition took 35 minutes. Stirring was then continued at +5° C. for 1 hour, and then at room temperature for a further hour, after which the mixture was heated to reflux under nitrogen for 20 hours. It was cooled to room temperature, and then the suspension was poured into a vigorously stirred mixture of water and ice (2.75 l) and concentrated hydrochloric acid (250 ml). A yellow solid was formed which is collected by filtration and washed in water (2 l). After drying under vacuum and on $P_2O_5$, 24.9 g of a yellow solid, 4,4-dimethyl-1-(3-nitro-phenyl-pyrazolidine- 3-one), was collected; yield 91%.

A suspension of this product (24.8 g; 105.5 mmol) in tetrahydrofuran (500 ml) was hydrogenated under 32 atmospheres of $H_2$ at 30° C. for 24 hours in the presence of palladium on a substrate of carbon (2 g at 10%). Magnesium sulphate (around 5 g) was added and the mixture was filtered under suction through a kieselguhr buffer. The filtrate was evaporated dry, producing a brown oil. A mixture of t-butanol (250 ml) and anhydrous THF (50 ml) was added. This solution was refluxed under dry nitrogen, while a solution of 1,3-propanesultone (12.9 g; 105.5 mmol) in anhydrous THF (30 ml) was added dropwise over around 40 minutes, whilst stirring. The mixture was refluxed under nitrogen for a further 20 hours. After cooling to room temperature, a solid was formed, which is collected by filtration and then dissolved again in acetonitrile (300 ml). This was filtered again and, after drying under vacuum, a cream-coloured solid (29.8 g) was obtained. By recrystallisation in a mixture of acetonitrile and ethanol and then drying under vacuum, 3-(4,4-dimethyl-3-oxo-pyrazolidine-1-yl)phenylamino-1-propanesulphonic acid (12.3 g; yield 36%) was obtained.

EXAMPLE 6

Slow Access—Ascorbic Acid Developing Agent Co-Developing Agent 12 or 14

In this example, film A was exposed at 2850 K with a color correction filter for ⅕sth of a second through a step tablet. This film was developed for 11 minutes at 23.5° C., was fixed for 5 minutes in T-MAX® fixer and was washed for 10 minutes under running water.

A developer solution according to the invention, comprising ascorbic acid as a developing agent and compound II or compound III as a co-developing agent, was assessed, comparing them with a KODAK D-76® powder universal developer which comprises hydroquinone and ELON® and with a second reference which comprises ascorbic acid and ELON®.

All the developers contained 45 mmol/l of developer, 12 mmol/l of co-developer and 126 g/l of potassium sulphite, and the pH was adjusted to 8.6 with potassium carbonate.

Figure 1:
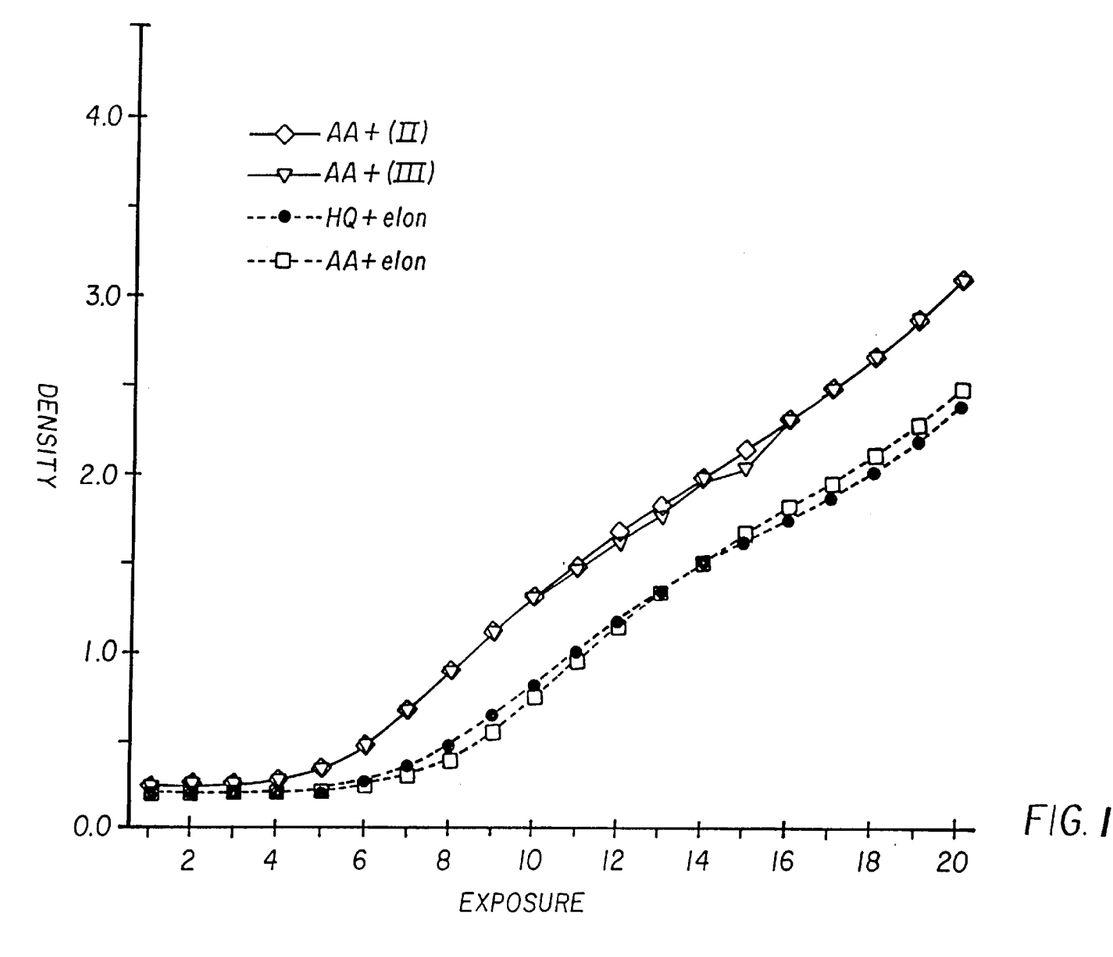
FIG. 1, which shows sensitometric curves obtained with reference developers and with developers according to the invention comprising ascorbic acid and compounds II or III in a "slow access" process for the development of a low-contrast black and white photographic film, or "film A".

FIG. 1 gives the sensitometric curves obtained with the two developers according to the invention and the reference developers. It can be seen that compounds II and III are more active than ELON® associated with ascorbic acid or hydroquinone.

EXAMPLE 7

Slow Access—Developers Which are Derivatives or Precursors of Ascorbic Acid—Co-Developing Agent 12

Solutions of developers according to the invention comprising as a developing agent L-ascorbic acid, D-isoascorbic acid, methyl-2 cetogluconate and 5,6-isopropylidene ascorbic acid and comprising compound II as a co-developing agent, were evaluated under the same conditions as in Example 6.

Figure 2:
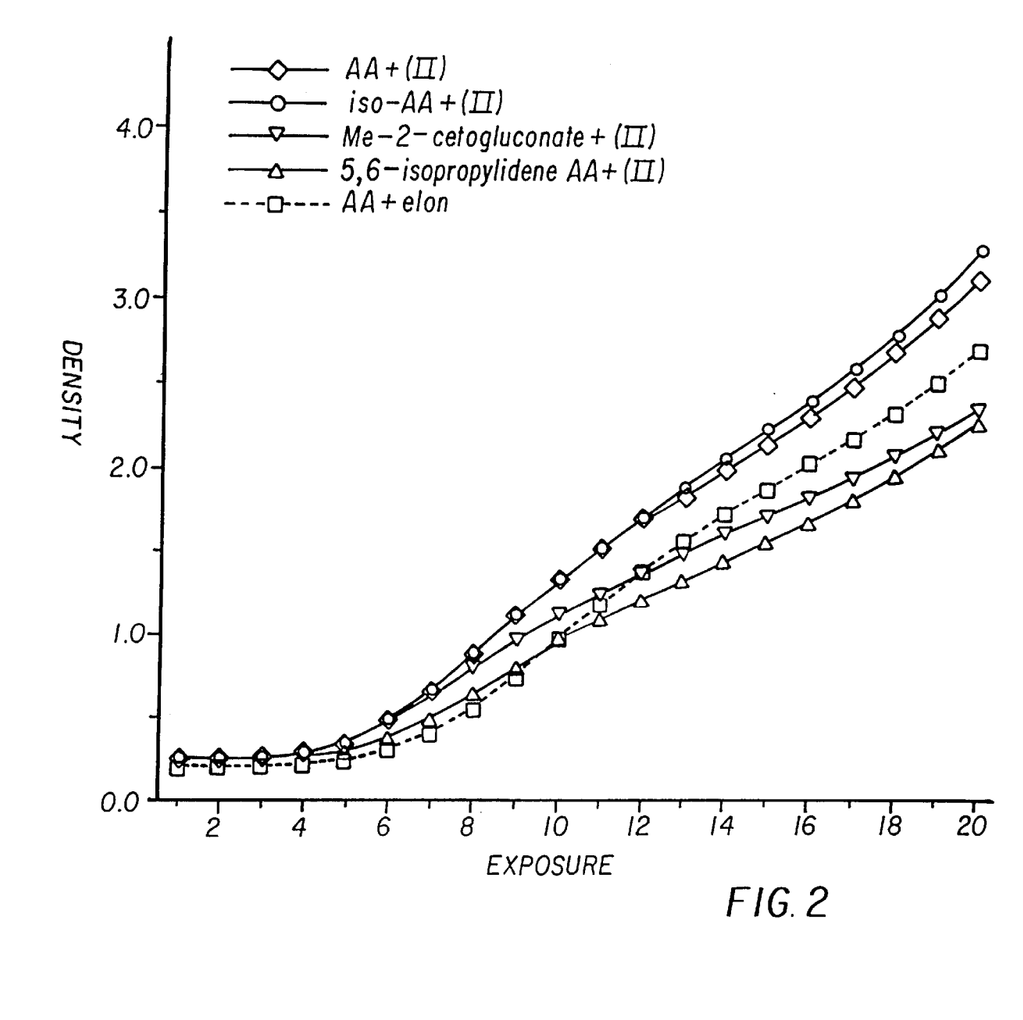
FIG. 2, which shows sensitometric curves obtained with developers according to the invention comprising ascorbic acid, its isomers, derivatives or precursors and compound II in a "slow access" process for the development of film A.

FIG. 2 gives the sensitometric curves obtained for a development time of 11 minutes at 23.5° C.

It can be seen that acceptable sensitometric results were obtained with all the derivatives or precursors of ascorbic acid in combination with compound II. It will also be observed that D-isoascorbic acid behaves in substantially the same way as L-ascorbic acid.

EXAMPLE 8

Rapid Access—Ascorbic Acid Developing Agent— Co-Developing Agent 12, 14 or 16

In this example, film B was exposed at 2850 K with a filter simulating the re-emission of a green screen for ⅕₀th of a second on both faces through a step tablet. This film was developed for 3 minutes at room temperature, manually reproducing the conditions of X-OMAT® processing machines, was fixed for 2 minutes and washed for 3 minutes in running water.

In this example the developer whose formula is given in *Research Disclosure* of August 1993, Article 35249 (already cited) was used as a reference:

| | |
|---|---|
| ascorbic acid | 32.0 g/l |
| dimezone-S (HMNP) | 2.5 g/l |
| Benzotriazole | 0.2 g/l |
| KBr | 4.0 g/l |
| $K_2SO_3$ | 50.0 g/l |
| $K_2CO_3$ | 100.0 g/l |
| Na DTPA* | 4.3 g/l |
| pH | 10.2 |

*DTPA is diethylenetriaminopentacetic acid

In the compositions according to the invention, dimezone-S was replaced with an equimolar quantity of compound II, III or IV.

Figure 3:
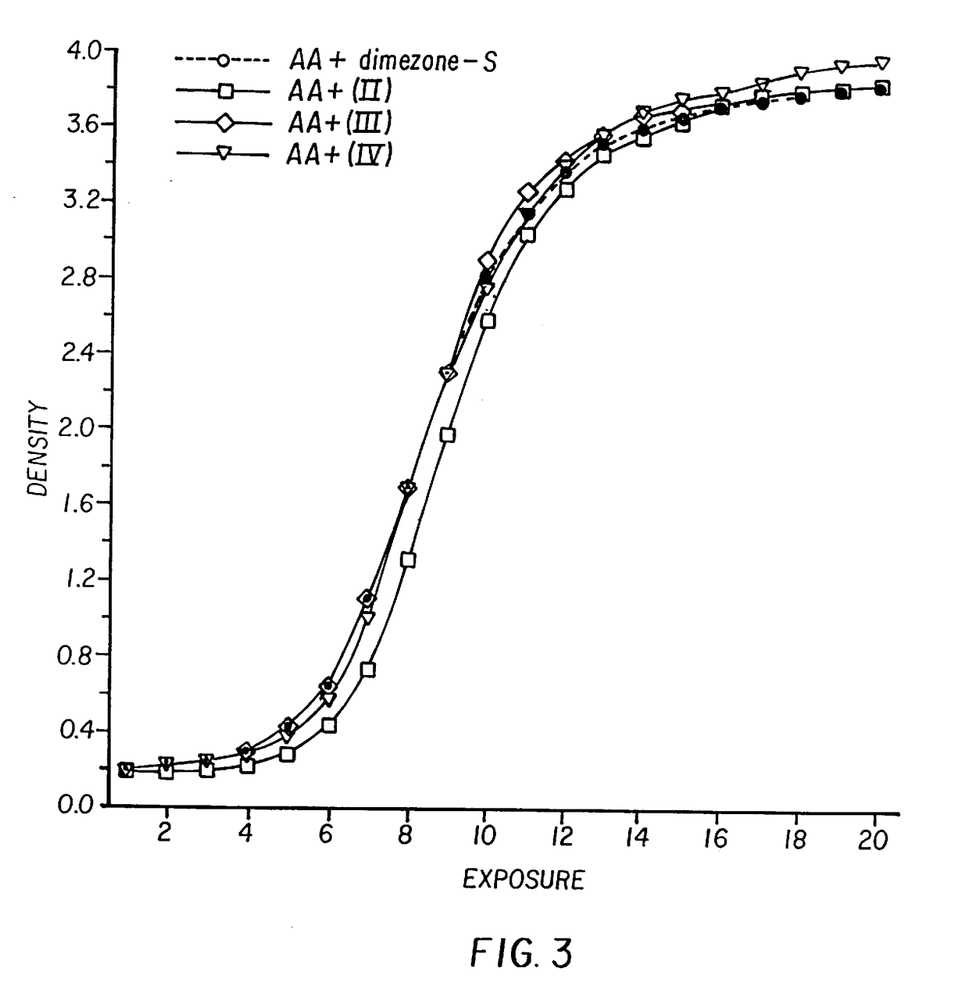
FIG. 3, which shows sensitometric curves obtained with a reference developer and with a developer according to the invention comprising ascorbic acid and compound II, III or IV in a "rapid access" process for the development of a film for medical radiography, or "film B".

FIG. 3 gives the sensitometric curves obtained. It can be seen that, in "rapid access", compounds II, III and IV combined with ascorbic acid give sensitometric results very close to those obtained with dimezone-S combined with ascorbic acid.

EXAMPLE 9

Rapid Access—Machine Processing—Ascorbic Acid Developing Agent—Co-Developing Agent 12

In this example, film B was exposed at 2850 K with a filter simulating the re-emission of a green screen for 1/50th of a second on both faces through a step tablet. This film was developed for 25 seconds at 35° C. in a KODAK X-OMAT® processing machine model ME-10.

In this example the reference developer of the previous example and a composition according to the invention containing ascorbic acid and compound II were used.

Figure 4:
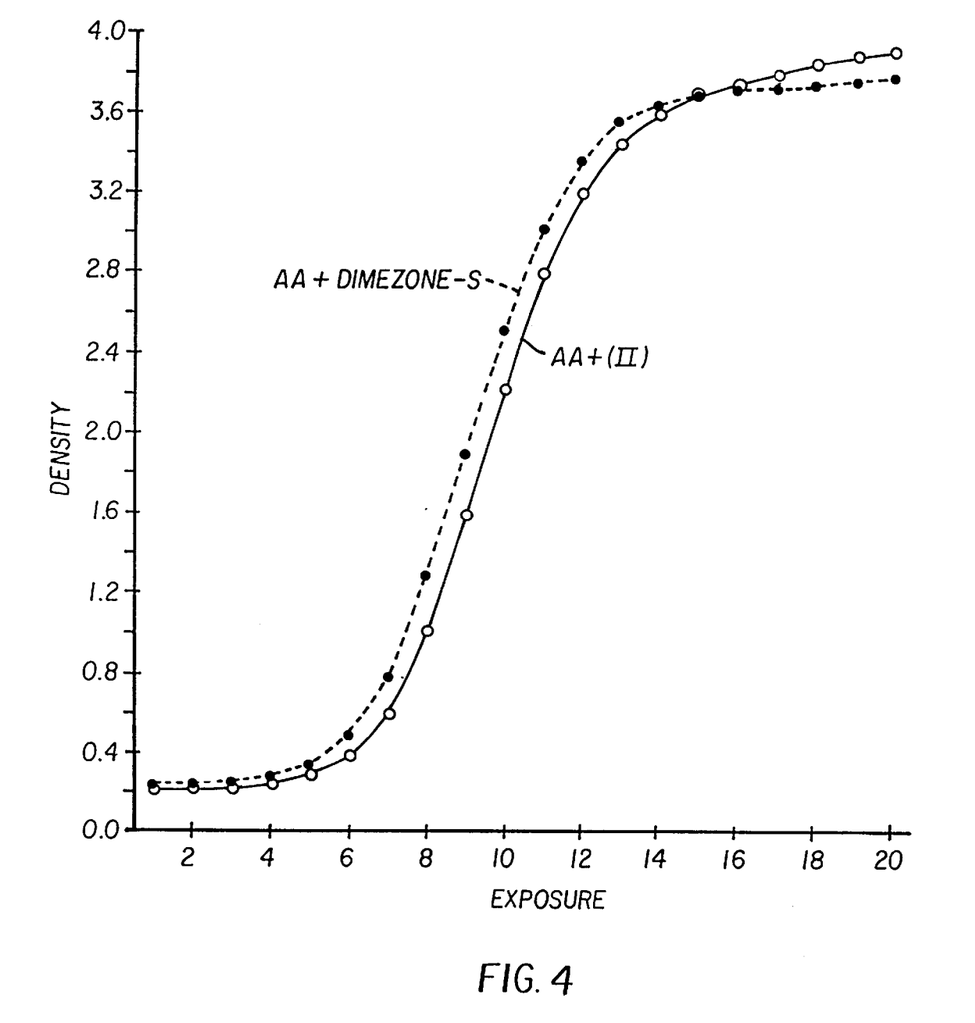
FIG. 4, which shows sensitometric curves obtained with a reference developer and with a developer according to the invention comprising ascorbic acid and compound II in a "rapid access" machine development process for the development of film B.

FIG. 4 gives the sensitometric curves obtained. It will be observed that the results obtained in an automatic machine at 35° C. satisfactorily reproduce the results of manual processing. In a machine, compound II combined with ascorbic acid gives, as in the previous example, sensitometric results very close to those obtained with dimezone-S combined with ascorbic acid.

EXAMPLE 10

Slow Access—Hydroquinone Developing Agent—Co-Developing Agent 12 or 14

Solutions of developers according to the invention comprising hydroquinone as a developing agent and compound II or III as the co-developing agent were evaluated under the same conditions as in Example 6, comparing them with the KODAK D-76® developer, which comprises hydroquinone and ELON®.

Figure 5:
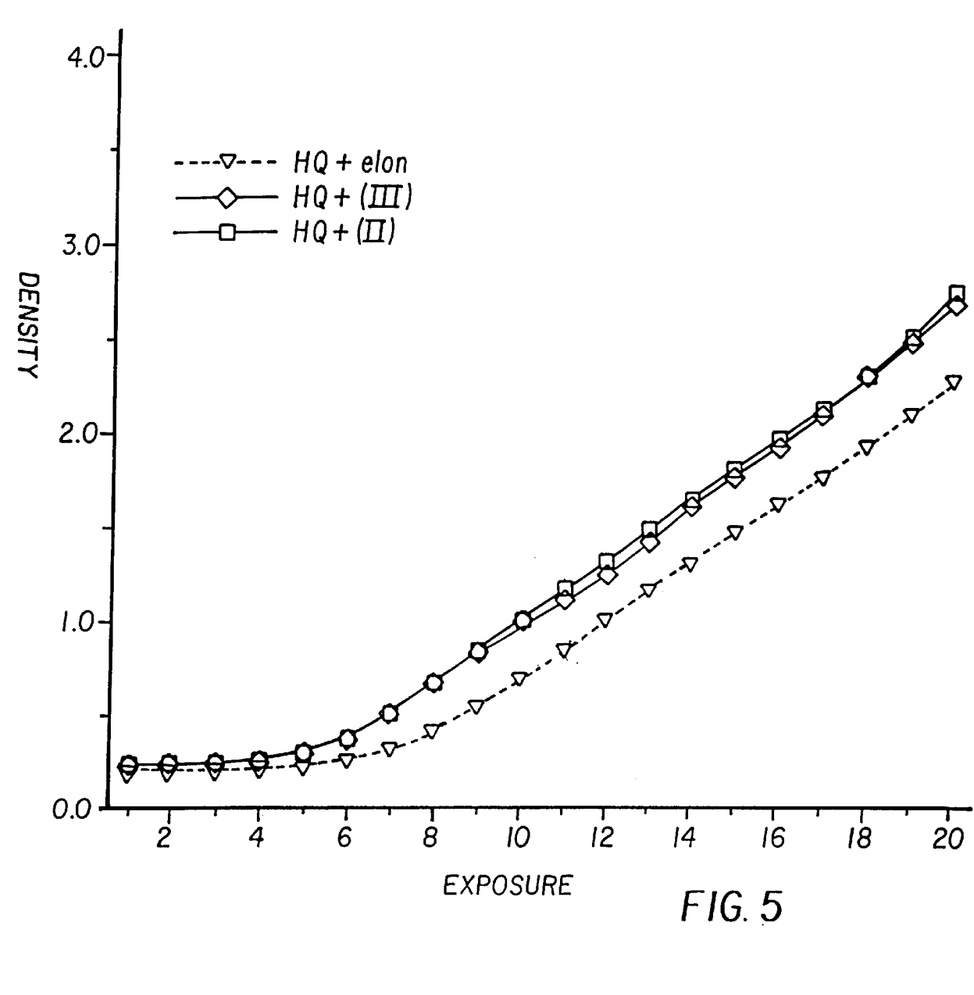
FIG. 5, which shows sensitometric curves obtained with a reference developer and with a developer according to the invention comprising hydroquinone and compounds II or III in a "slow access" process for the development of film A®.

FIG. 5 gives the sensitometric curves obtained for a development time of 11 minutes at 23.5° C. It can be seen that compounds II and III are more active than ELON® when they are combined with hydroquinone.

EXAMPLE 11

Rapid Access—Hydroquinone Developing Agent—Co-Developing Agent 12

In this example, film C was developed under the same conditions as in Example 8, using as a reference the RP X-OMAT® developer comprising hydroquinone and phenidone-A and two developers according to the invention comprising hydroquinone and compound II or III.

Figure 6:
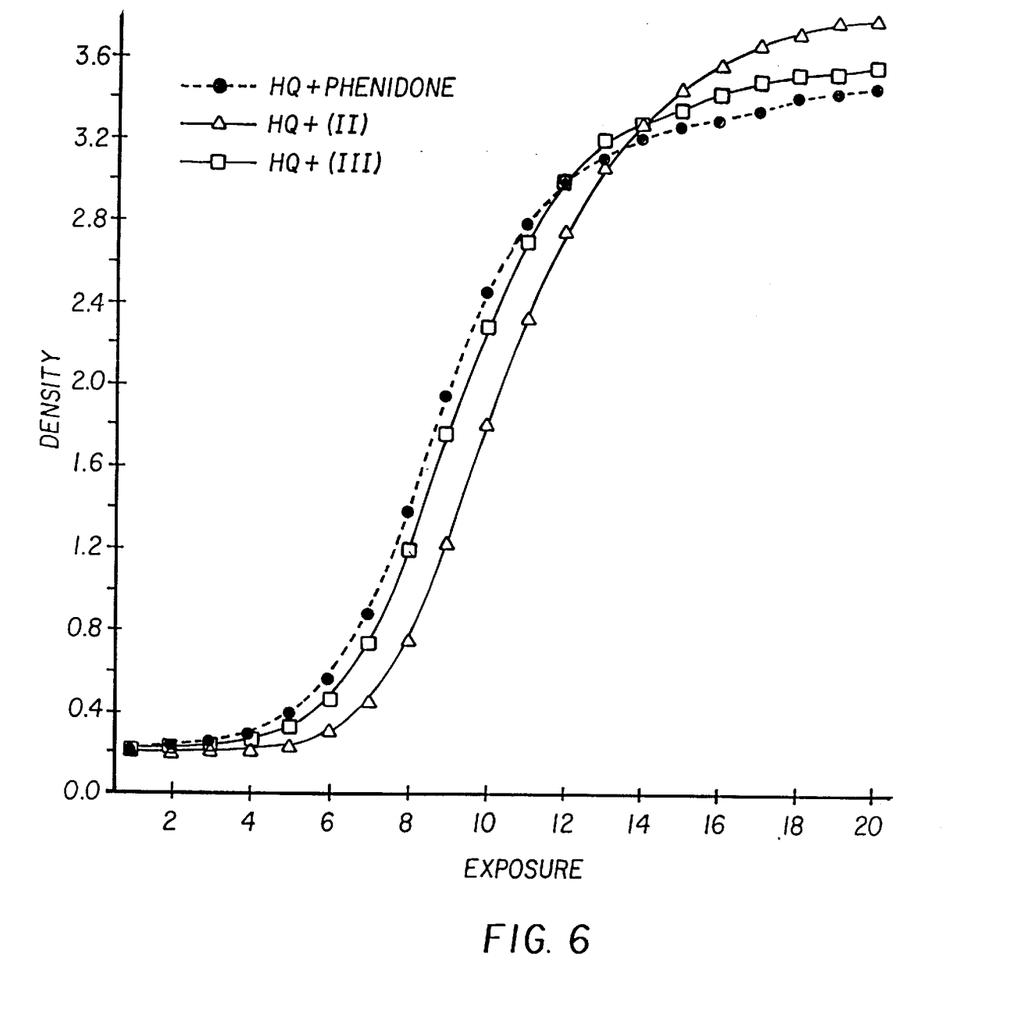
FIG. 6, which shows sensitometric curves obtained with a reference developer and with a developer according to the invention comprising hydroquinone and, as a co-developer, compounds II and III in a "rapid access" process for the development of a film for medical radiography or "film C".

It can be seen in FIG. 6 that in "rapid access" mode compounds II or III associated with hydroquinone give a sensitometry very close to that obtained with hydroquinone combined with phenidone-A.

The invention has been described in detail with particular reference to preferred embodiments thereof, but it will be understood that variations and modifications can be effected within the spirit and scope of the invention.

We claim:

1. An aqueous developer solution comprising:
   a silver halide developing agent selected from reductones and compounds of the hydroquinone type, and
   at least one co-developing agent of the formula I:

wherein $R_1$ and $R_2$ are independently alkyl, or a group represented by the formula II:

wherein m is an integer of 0 to 5, and n is 0 or 1, L is a divalent group selected from wherein $R_8$ is $R_9$ or —A—(Sol), $R_9$ is hydrogen, alkyl or aryl;

A is a divalent group selected from wherein q is an integer of 0 to 5, and y is an integer of 1 to 3;

(Sol) is a solubilizing group selected from:

polyhydroxyalkyl, wherein $R_{10}$ is alkyl or aryl, $R_{11}$ is hydroxy, alkyl or aryl and $R_{12}$ is hydrogen, alkyl or aryl;

$R_3$ to $R_7$ in formula (I) are independently hydrogen, alkyl, alkoxy, aryloxy, or a group represented by the formula:

wherein p is 0 or 1;

X is a divalent group selected from —O—, —S— and —NR$_8$—; and m, L, n, A, (Sol) and $R_8$ are as defined above, provided that at least one of the radicals $R_1$ to $R_7$ comprises Sol.

2. The aqueous developer solution of claim 1 wherein $R_1$ and $R_2$ are independently alkyl or substituted alkyl, and at least one of $R_3$ to $R_7$ is the group represented by the formula:

wherein p, m and n are each 0, A represents or phenylene.

3. The aqueous developer solution of claim 1 wherein $R_1$ and $R_2$ are independently alkyl or substituted alkyl, and at least one of $R_3$–$R_7$ is the group represented by the formula:

where p and m are each 0, A represents or phenylene; and L represents wherein $R_8$ and $R_9$ are each hydrogen.

4. The aqueous developer solution of claim 1 wherein $R_3$–$R_7$ are independently alkyl, substituted alkyl, alkoxy or substituted alkoxy.

5. The aqueous developer solution of claim 1, in which said silver halide developing agent is ascorbic acid, a sugar-type derivative of ascorbic acid, or a stereoisomer, diastereoisomer or precursor of one of these acids or their salts.

6. The aqueous developer of claim 5 in which said silver halide developing agent is ascorbic acid, D-isoascorbic acid, methyl-2-cetogluconate or 5,6-isopropylene ascorbic acid.

7. A method for providing an image comprising contacting an imagewise exposed photographic silver halide material with the aqueous developer solution of claim 1.

8. The process of claim 7 wherein said contacting step lasts for less than 1 minute.

* * * * *